(12) United States Patent
Hino

(10) Patent No.: US 6,206,523 B1
(45) Date of Patent: Mar. 27, 2001

(54) EYE REFRACTIVE POWER MEASUREMENT APPARATUS

(75) Inventor: Toshiya Hino, Toyohashi (JP)

(73) Assignee: Nidek Co., Ltd., Aichi (JP)

( * ) Notice: Subject to any disclaimer, the term of this patent is extended or adjusted under 35 U.S.C. 154(b) by 0 days.

(21) Appl. No.: 09/512,316

(22) Filed: Feb. 24, 2000

(30) Foreign Application Priority Data

Feb. 26, 1999 (JP) .................................................. 11-050394

(51) Int. Cl.$^7$ ........................................................ A61B 3/10
(52) U.S. Cl. .................................................................. 351/212
(58) Field of Search .................................. 351/208, 211, 351/212, 221, 245, 205

(56) References Cited

U.S. PATENT DOCUMENTS

| | | | |
|---|---|---|---|
| 5,751,396 | * 5/1998 | Masuda et al. | 351/221 |
| 5,907,388 | 5/1999 | Fujieda . | |

FOREIGN PATENT DOCUMENTS

| | | |
|---|---|---|
| 3-128034 | 5/1991 | (JP) . |
| 6-245909 | 9/1994 | (JP) . |
| 7-222716 | 8/1995 | (JP) . |

\* cited by examiner

Primary Examiner—George Manuel
(74) Attorney, Agent, or Firm—Finnegan, Henderson, Farabow, Garrett & Dunner, L.L.P.

(57) ABSTRACT

An eye refractive power measurement apparatus for measuring refractive power of an eye to be examined, comprises a measurement unit including a projecting optical system for projecting measurement light onto a fundus of the eye and a detecting optical system for receiving the reflected light of the measurement light reflected from the fundus, an arithmetic unit for obtaining the refractive power based on an output signal from the photodetector, a moving unit for moving the measurement unit relative to the eye, and a control unit for detecting an interfering part that interferes with the reflected light passing through the eye based on the output signal from the photodetector and for driving and controlling the moving unit based on the detected results.

16 Claims, 4 Drawing Sheets

EYE REFRACTIVE POWER MEASUREMENT APPARATUS

BACKGROUND OF THE INVENTION

1. Field of the Invention

The present invention relates to an eye refractive power measurement apparatus for measuring refractive power of an eye to be examined.

2. Description of Related Art

Widely known is an eye refractive power measurement apparatus comprises a measuring optical system which projects measurement light onto a fundus of an eye to be examined and receives the light reflected therefrom with a photodetector in order to obtain the refractive power based on output signals from the photodetector. In the measurement with this apparatus, a measurement error often occurs due to partial opacity of ocular media (crystalline lens and the like) caused by cataract and the like.

In order to carry out measurement on this type of the eye that often causes a measurement error, a measurement optical system needs to be re-aligned at such a position to avoid an opaque area and the like, a part that interferes with the measurement while observing the eye to be examined.

However, it is difficult especially for an examiner who is unfamiliar with the examination to find such an appropriate position.

SUMMARY OF THE INVENTION

The present invention has been made in view of the above circumstances and has an object to overcome the above problems and to provide an eye refractive power measurement apparatus with which an examiner can carry out measurement easily in such a position to avoid a part such as opacity and the like.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the present invention, as embodied and broadly described herein, an eye refractive power measurement apparatus for measuring refractive power of an eye to be examined, the apparatus comprises a measurement unit including a projecting optical system for projecting measurement light onto a fundus of the eye, and a detecting optical system for receiving the reflected light of the measurement light reflected from the fundus, an arithmetic unit for obtaining the refractive power based on an output signal from the photodetector, a moving unit for moving the measurement unit relative to the eye, and a control unit for detecting an interfering part that interferes with the reflected light passing through the eye based on the output signal from the photodetector and for driving and controlling the moving unit based on the detected results.

In another aspect of the present invention, an eye refractive power measurement apparatus for measuring refractive power of an eye to be examined, the apparatus comprises measurement means for projecting measurement light onto a fundus of the eye, and thereby receiving the reflected light of the measurement light reflected from the fundus with a photodetector, arithmetic means for obtaining the refractive power based on an output signal from the photodetector, moving means for moves the measurement means relative to the eye, detecting means for detecting an interfering part that interferes with the reflected light passing through the eye based on the output signal from the photodetector, and control means for driving and controlling the moving means based on the detected results obtained by the detecting means.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1:
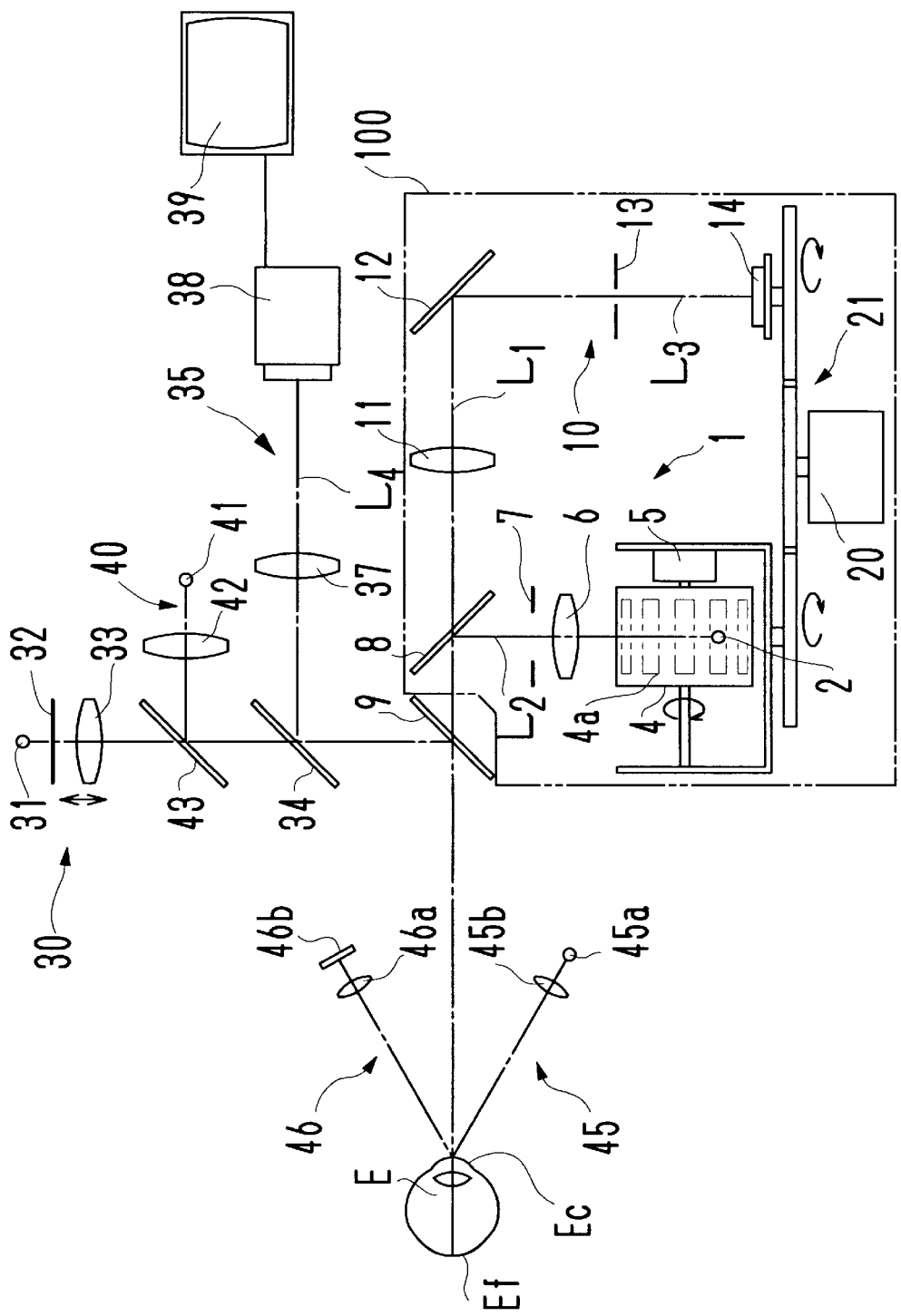
FIG. 1 is a view showing a schematic configuration of an optical system of the apparatus according to the invention.

A detailed description of one preferred embodiment of an eye refractive power measurement apparatus embodying the present invention will now be given referring to the accompanying drawings. FIG. 1 is a view showing a schematic configuration of an optical system of the apparatus according to the invention.

Eye Refractive Power Measurement Optical System

An eye refractive power measurement optical system 100 comprises a slit light projecting optical system 1 and a slit image detecting optical system 10. The projecting optical system 1 has a configuration as follows. Reference numeral 2 is a light source that emits near infrared light. 4 is a cylindrical-shaped rotation sector, which can be rotated in a fixed direction with a fixed velocity by a motor 5, and which has a number of slit apertures 4a formed through the lateral surface thereof. 6 is a projecting lens. The light source 2 is placed at a conjugate position with a vicinity of a cornea Ec of an eye E relative to the lens 6. 7 is a limit aperture and 8 is a beam splitter for making an optical axis L2 of the projecting optical system 1 coaxial with a principal optical axis L1, which is opposed to the eye E.

The near infrared light emitted from the light source 2 illuminates the slit apertures 4a formed through the surface of the rotation sector 4, thereby scanning slit-shaped light. The slight-shaped light passes through the lens 6 and the diaphragm 7, and is reflected by the beam splitter 8. Thereafter, the slit-shaped light passes through a beam splitter 9 and converges in the vicinity of the cornea Ec, thereby being projected onto a fundus Ef of the eye E.

Figure 5A:
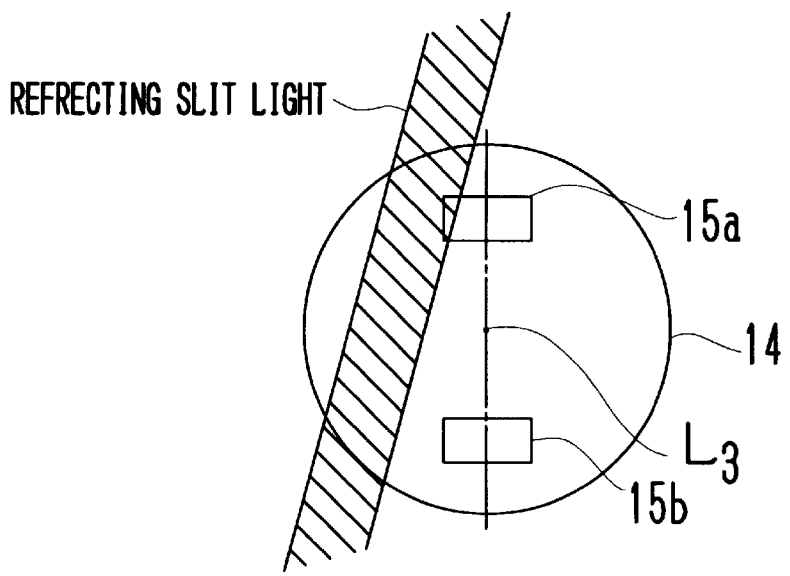
FIGS. 5A–5C are views showing arrangement examples of the photodetectors.
Figure 5B:
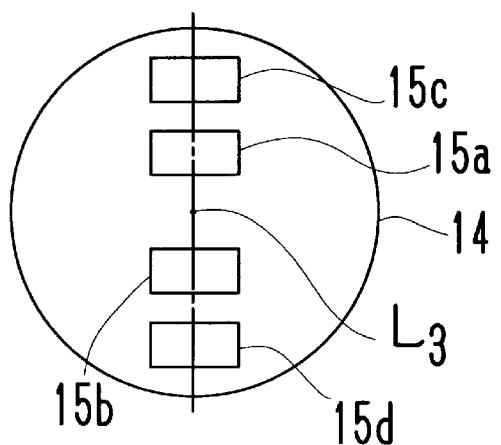
Figure 5C:
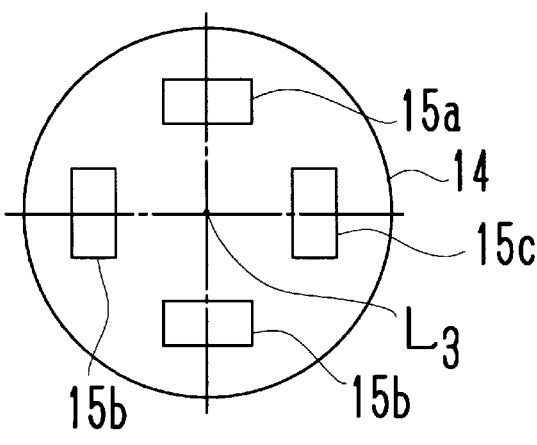

The detecting optical system 10 comprises a receiving lens 11 and a mirror 12, both of which are located on the principal optical L1, as well as a diaphragm 13 and a light receiving unit 14, both of which are located on an optical axis L3 of light reflected by the mirror 12. The diaphragm 13 is located at a back focal point of the lens 11 on which it focuses via the mirror 12. The light receiving unit 14 comprises, on its light receiving surface, a pair of photodetectors 15a and 15b at an approximately conjugate position with the cornea Ec relative to the lens 11. In addition, the photodetectors 15a and 15b are disposed symmetric with each other relative to the optical axis L3 (see FIG. 5A) to be capable of measuring an eye refractive power of a pupil of 2.5 mm in diameter. Further, different from this embodiment and as fully disclosed in U.S. Pat. No. 5,907,388 (JP Publication Nos. HEI 10 (1998)-108336 and HEI 10 (1998)-108837) by the present applicant, a plurality of pairs of photodetectors may be disposed on one meridian (see FIG. 5B), or one pair of photodetectors may be disposed on a plurality of meridians (see FIG. 5C). (It is needless to say that a plurality of photodetectors may be disposed on a plurality of meridians.) In the case of disposing a plurality of photodetectors on a plurality of meridians, slit apertures formed through the surface of the sector 4 should be oriented in a plurality of directions (see U.S. Pat. No. 5,907,388). 15c and 15d shown in FIGS. 5B and 5C also denote photodetectors.

In the measurement optical system 100 having the above-described configuration, a rotation mechanism 21 comprising a motor 20, a gear and the like rotates components of the light projecting optical system 1, namely the light source 2 through motor 5, on the optical axis L2, and rotates the light receiving unit 14 on the optical axis L3 in synchronism. Here, the direction in which the photodetectors 15a and 15b are disposed on the light receiving unit 14 is set so that it coincides with the scanning direction of the slit light projected onto the eye E by the projecting optical system 1.

Fixation Target Optical System

Reference numeral 30 is a fixation target optical system, 31 is a light source for emitting visible light, 32 is a fixation target and 33 is a projecting lens. The lens 33 fogs the eye E by moving in the direction axially of the optical axis. The light source 31 illuminates the fixation target 32 with visible light, and the visible light from the fixation target 32 passes through beam splitters 43 and 34 and then is reflected by the beam splitter 9 toward the eye E. As the result, the eye E fixates on the fixation target 32.

Alignment Optical System

Reference numeral 40 is a front target projecting optical system for projecting a front alignment target that is used to detect a right-and-left direction as well as an up-and-down direction (X and Y directions) from front of the eye E. The near infrared light emitted from a light source 41 is made approximately parallel light by passing through a lens 42, and then projected onto the eye E via the beam splitters 43, 34 and 9.

Further, reference numeral 45 is a distance target projecting optical system for projecting a distance alignment target that is used to detect a back-and-forth direction (Z direction). The near infrared light emitted from a light source 45a is made approximately parallel light by passing through a lens 45b, and then projected onto the cornea Ec from a slanting direction. 46 is a distance target detecting optical system. The light projected by the projecting optical system 45 is reflected by the cornea Ec and enters into a one-dimensional position detecting element 46b via a lens 46a. When the eye E moves in the Z direction, an image of the distance target formed on the cornea Ec moves on the detecting element 46b. Consequently, the alignment condition of the eye E in Z direction is detected from the displacement of the image. Detection of the alignment condition in x and Y directions may be done as follows: the X direction may be detected from an image of a luminance point illuminated by an anterior eye segment illumination light source (not illustrated); and the Y direction may be detected from an image of a luminance point illuminated by the aforementioned projecting optical system 45.

Observation Optical System

Reference numeral 35 is an observation optical system, and a photographing lens 37 and a CCD camera 38 are disposed on the reflecting side of the beam splitter 34 along an optical axis L4. An image of the anterior segment of the eye E illuminated by the unillustrated anterior eye segment illumination light source is formed on a surface of an image-pickup element of the camera 38 via the beam splitters 9 and 34 and the lens 37, thereby being displayed on a TV monitor 39. The observation optical system 35 also functions as an optical system for detecting an image of the front target formed on the cornea Ec by the projecting optical system 40. The alignment condition in the right-and-left direction and the up-and-down direction (X and Y directions) is detected from the position of the image of the front target photographed by the camera 38.

Figure 2:
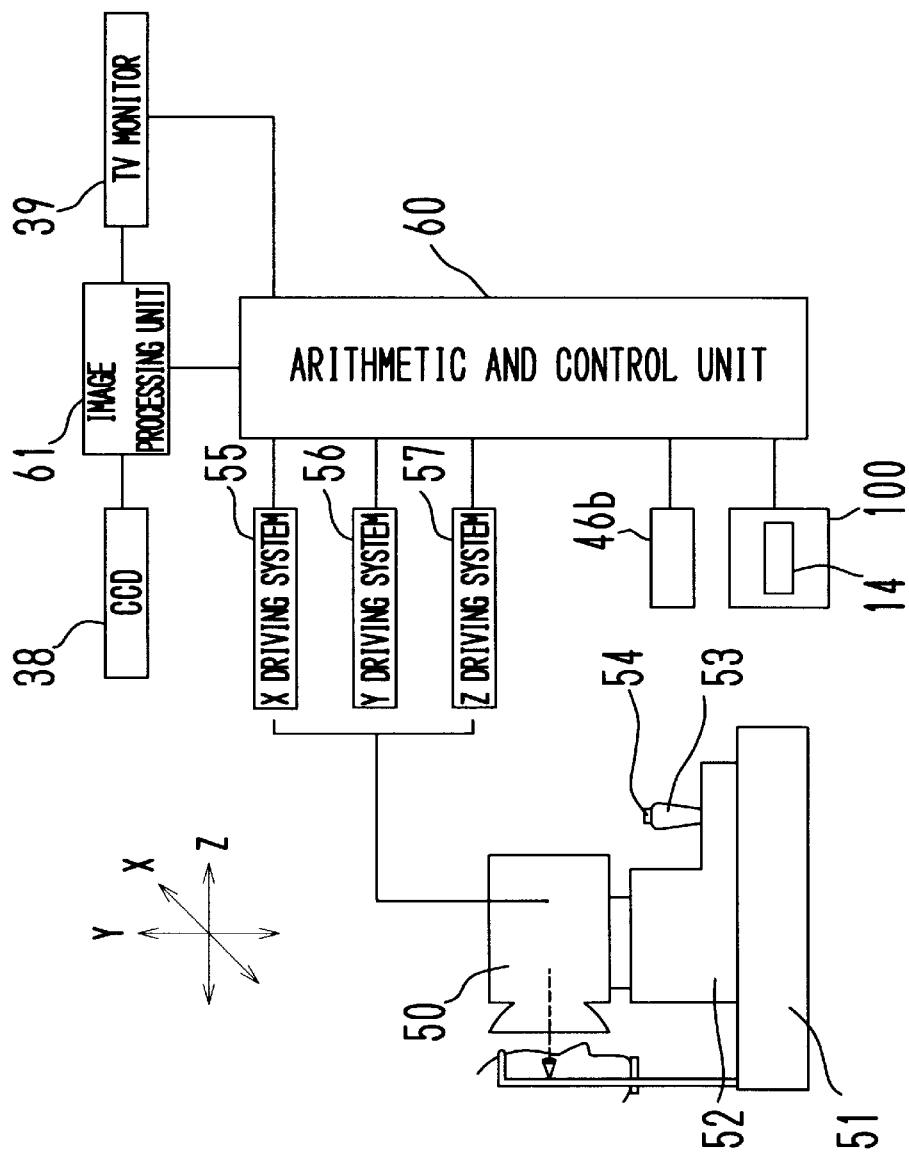
FIG. 2 is a block diagram showing major parts of a control system of the apparatus.

FIG. 2 is a block diagram showing major parts of a control system of the apparatus. A measurement part 50 having the optical systems shown in FIG. 1 is movable in X (right-and-left) direction, Y (up-and-down) direction and Z (back-and-forth) direction respectively by an X driving system 55, a Y driving system 56 and a Z driving system 57 relative to a movable platform 52 which is horizontally slidable on a base 51 of the apparatus. Each of the driving systems 55, 56 and 57 comprises a motor, a sliding mechanism and the like, and is controlled its drive by an arithmetic and control unit 60. 54 is a measurement start switch mounted at the top of a joystick 53.

Reference numeral 61 is an image processing unit that detects an image of the front target photographed by the camera 38, upon observation, and inputs the detected result to the arithmetic and control unit 60. Based on the inputted signals indicating the detected result, the arithmetic and control unit 60 judges the alignment condition of the apparatus (the measurement unit 50) in X and Y directions with respect to the eye E.

Hereinafter, operations of the apparatus having the aforementioned configuration will be described. The image of the anterior eye segment photographed by the camera 38 is displayed on the monitor 39. While observing the image of the anterior eye segment displayed on the monitor 39, an examiner makes rough alignment with operating the joystick 53 and the like. Once the image of the front target formed on the eye E is detected by the image processing unit 61, the arithmetic and control unit 60 controls drive of the X driving system 55 and the Y driving system 56, thereby moving the measurement unit 50 to achieve a predetermined alignment condition. Detected signals indicative of the image of the distance target detected by a detecting element 46b is inputted to the arithmetic and control unit 60. Based on the signals, the arithmetic and control unit 60 controls drive of the Z direction driving system, whereby the measurement unit 50 moves back and forth to achieve an appropriate alignment condition in the Z direction.

Once it is judged that the alignment condition in X, Y and Z directions is appropriate, the arithmetic and control unit 60 generates a trigger signal so that the fixation target optical system 30 and the measurement optical system 100 go in to action to measure the refractive power. First, the arithmetic and control unit 60 obtains refractive power through a preliminary measurement based on phase difference signals sent from the photodetectors 15a and 15b. In accordance with the result, the lens 33 included in the fixation target optical system 30 is moved to perform fogging of the eye E.

With the eye E being fogged, the projecting optical system 1 and the light receiving unit 14 are rotated 180° in predetermined angle steps. The refractive power in each meridian direction is obtained from the phase difference signals sent from the photodetectors 15a and 15b being rotated. Through conducting a predetermined process on the thus obtained refractive power, the spherical power (S), the cylindrical power (C) and the axial angle (A) are obtained.

In such measurement, if opacity is present in a crystalline lens, or if such factors as eyelashes or corneal injury that interfere with the measurement are present, drastically low amount of the light that is reflected from fundus reaches the photodetectors 15a and 15b. As the result, the eye refractive power in the direction where the photodetectors 15a and 15b are positioned can not be obtained. Consequently, neither S, C nor A can be calculated, thereby causing a measurement error. Also, an measurement error may occur similarly in the case where the eye to be examined has a pupil that is of asymmetric shape with respect to the corneal center.

Figure 3:
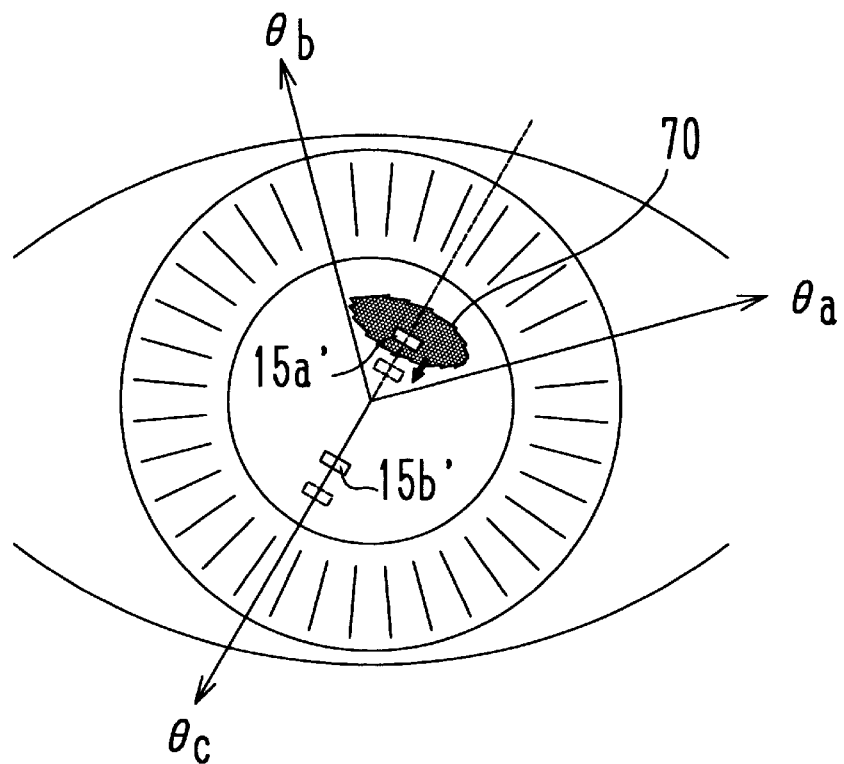
FIG. 3 is a view showing an example that an opaque area spreads out in a measurement area of the eye.
Figure 4:
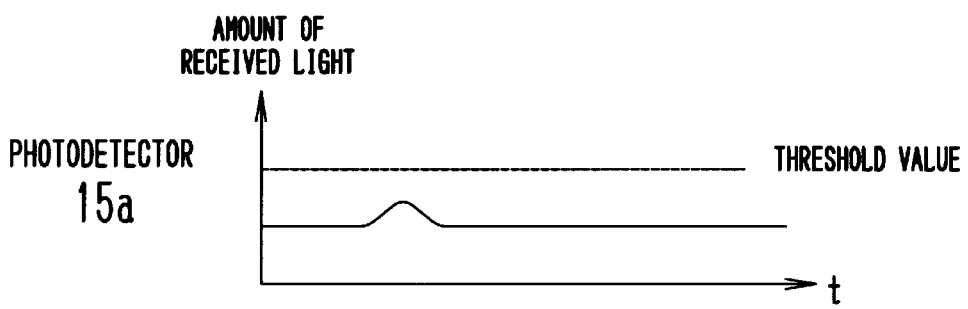
FIG. 4 is a view showing variation in amount of light that a photodetector receives, when the photodetector is positioned in an angular region where an opaque area spreads out.
Figure 4:
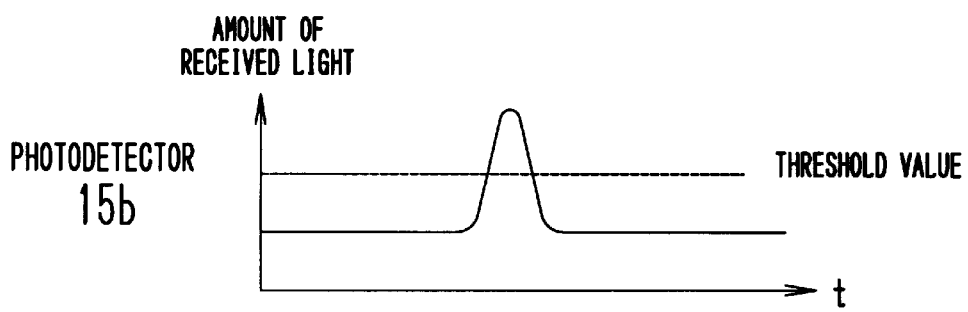

FIG. 3 is a view showing an example that an opaque area 70 spreads out in a measurement area of the eye. Reference numerals 15a' and 15b' in the figure schematically illustrate the positional relationship in the case of projecting the photodetectors 15a and 15b on the cornea (on the pupil) when they are positioned within an area corresponding to an angular region in which the opaque area 70 spreads out. Further, FIG. 4 is a view showing variation in the amount of light that each photodetector receives, when the photodetectors are positioned as shown in FIG. 3. If the level of the amount of light received by the photodetector 15a is lower than a threshold value for the measurement, the phase difference method is not capable of obtaining the refractive power in the meridian direction extending in the angular region where the opaque area 70 spreads out.

When the measurement error occurs, the arithmetic and control unit 60 automatically moves the measurement optical system 100 to a position where the opaque area 70 is avoided in the following way. Since the measurement is repeatedly performed in the predetermined angle steps while rotating the light receiving unit 14 180°, information about the angle at which the amount of received light decreases is obtained based on the signals indicative of the received light. In the example shown in FIG. 3, when the photodetector 15a fails to receive the light in the amount equal to, or greater than the threshold value in the angular region formed between θa–θb, it is determined that the opaque area 70, which is the factor of cutting off the measurement light is present in this region. In this case, the measurement optical system 100 should be moved in the direction of the angle θc that is opposite to the center of the angle between θa–θb so that the opaque area 70 can be avoided most effectively. The arithmetic and control unit 60 obtains the angle θc, and moves the measurement unit 50 in the X and Y directions from its position at the time of the aliment completion. The amount of the movement that the measurement unit 50 makes in order to avoid the opaque area 70 may be preliminary determined to be 0.5 mm or 1 mm. Alternatively, the image processing unit 61 obtains the shape of the pupil from the image of the anterior eye segment, and the movement may be made based on that information within a range where the measurement light (the light reflected from the fundus) is not eclipsed by the pupil.

As described above, the arithmetic and control unit 60 moves the measurement unit 50 relative to the eye E, and then starts the measurement automatically. Here, if a measurement error occurs again, the measurement unit 50 is further moved within a measurement permissible range and then performs the measurement. In the case where the number of the measurement errors exceeds a predetermined number, there is a strong possibility that the area interfering with the measurement is large, or the errors are due to another factor. Therefore, the situation is displayed on the monitor 39 to inform the examiner.

It should be noted that in the case the measurement unit 50 is moved to adjust its position in order to avoid the measurement interfering area, the thus obtained measurement results tend to be less accurate to some extent comparing to the case where the alignment is completed with respect to the corneal center. Yet, it is far more useful than not obtaining any measurement results at all due to the measurement error. The thus obtained measurement results may be used, for example, as initial data for performing subjective optometry.

In addition, in the case where the measurement error occurs, the angular region that interferes with the measurement is calculated as described above. If the information about the angle is displayed together with the measurement results, the information can be even more useful.

In the embodiment described above, the apparatus is operated by the examiner. However, the present invention is especially effective in the case where the apparatus is configured to be operatable without an examiner.

As described above, according to the present invention, the measurement is easily carried out with avoiding occurrence of a measurement error even when an eye to be examined has a part that interferes with the measurement. According to the present invention, in addition, positional adjustment is made automatically to avoid an measurement error, and therefore even an examiner who is unaccustomed to operating the apparatus can carry out the measurement smoothly.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An eye refractive power measurement apparatus for measuring refractive power of an eye to be examined, comprising:

a measurement unit including a projecting optical system which is provided with a light source for projecting measurement light onto a fundus of the eye, and a detecting optical system which is provided with at least one photodetector for receiving the reflected light of the measurement light reflected from the fundus;

an arithmetic unit, which is connected to the photodetector, for obtaining the refractive power based on an output signal from the photodetector;

a moving unit for moving the measurement unit relative to the eye; and a control unit, which is connected to the photodetector and to the moving unit, for detecting an interfering part that interferes with at least one of the measurement light and the reflected light based on the output signal from the photodetector, and for driving and controlling the moving unit based on the detected results.

2. The eye refractive power measurement apparatus according to claim 1, wherein the control unit drives and controls the moving unit, thereby moving the measurement unit so as not to place the photodetector at a position corresponding to the detected interfering part.

3. The eye refractive power measurement apparatus according to claim 1, wherein the control unit detects the interfering part through detecting angle information, and drives and controls the moving unit based on the detected angle information.

4. The eye refractive power measurement apparatus according to claim 3, wherein the control unit detects the interfering part through detecting the angle information about a radial angle whose center is at an approximate corneal center, obtains angle information indicating a moving direction from the detected angle information, and controls the moving unit based on the thus obtained angle information indicating the moving direction.

5. The eye refractive power measurement apparatus according to claim 1, wherein the measurement unit includes an alignment optical system for detecting an alignment condition of the measurement unit relative to the eye, and the control unit drives and controls the moving unit based on the detected result obtained by the alignment optical system, so that the measurement unit is moved to have a predetermined positional relationship with the eye.

6. The eye refractive power measurement apparatus according to claim 1, wherein the projecting optical system includes a scan unit for shaping the measurement light from the light source into slit light, and for projecting the slit light in a manner that the slit light scans over the fundus, and the detecting optical system includes a light receiving unit having at least one pair of the photodetectors for receiving the slit light reflected from the fundus and arranged symmetric about an optical axis at an approximately conjugate position with the cornea of the eye.

7. The eye refractive power measurement apparatus according to claim 6, wherein at least one pair of the photodetectors is arranged along one and the same meridian, and the measurement unit includes a rotation unit for rotating the scan unit and the light receiving unit on each optical axis in synchronism.

8. The eye refractive power measurement apparatus according to claim 6, wherein at least one pair of the photodetectors is arranged along each of a plurality of meridians.

9. An eye refractive power measurement apparatus for measuring refractive power of an eye to be examined, comprising:

measurement means for projecting measurement light onto a fundus of the eye, and thereby receiving the reflected light of the measurement light reflected from the fundus with a photodetector;

arithmetic means for obtaining the refractive power based on an output signal from the photodetector;

moving means for moving the measurement means relative to the eye;

detecting means for detecting an interfering part that interferes with at least one of the measurement light and the reflected light based on the output signal from the photodetector; and control means for driving and controlling the moving means based on the detected results obtained by the detecting means.

10. The eye refractive power measurement apparatus according to claim 9, wherein the control means drives and controls the moving unit, thereby moving the measurement means so as not to place the photodetector at a position corresponding to the interfering part detected by the detecting means.

11. The eye refractive power measurement apparatus according to claim 9, wherein the detecting means detects the interfering part through detecting angle information, and the control means drives and controls the moving means based on the detected angle information.

12. The eye refractive power measurement apparatus according to claim 11, wherein the detecting means detects the interfering part through detecting the angle information about a radial angle whose center is approximately at a corneal center, and the control means obtains angle information indicating a moving direction from the detected angle information, and controls the moving means based on the thus obtained angle information indicating the moving direction.

13. The eye refractive power measurement apparatus according to claim 9, further comprising alignment means for detecting an alignment condition of the measurement means relative to the eye, and wherein the control means drives and controls the moving means based on the detected results obtained by the alignment means, so that the measurement means is moved to have a predetermined positional relationship with the eye.

14. The eye refractive power measurement apparatus according to claim 9, wherein the measurement means includes:

a projecting optical system for shaping the measurement light into slit light, and for projecting the slit light in a manner that the slit light scans over the fundus;

a detecting optical system which is provided with at least one pair of photodetectors for receiving the slit light reflected from the fundus and arranged symmetric about an optical axis at an approximately conjugate position with the cornea of the eye.

15. The eye refractive power measurement apparatus according to claim 14, wherein at least one pair of the photodetectors is arranged along one and the same meridian, and the measurement means includes rotation means for rotating the projecting optical system and the detecting optical system on each optical axis in synchronism.

16. The eye refractive power measurement apparatus according to claim 14, wherein at least one pair of the photodetectors is arranged along each of a plurality of meridians.

* * * * *